United States Patent [19]
Valenti

[11] Patent Number: 5,772,753
[45] Date of Patent: Jun. 30, 1998

[54] CEMENT ACCELERATORS

[75] Inventor: Salvatore Valenti, Binningen, Switzerland

[73] Assignee: MBT Holding AG, Zurich, Switzerland

[21] Appl. No.: 754,954

[22] Filed: Nov. 21, 1996

[30] Foreign Application Priority Data

Nov. 23, 1995 [GB] United Kingdom .................. 9524002
Dec. 1, 1995 [GB] United Kingdom .................. 9524577

[51] Int. Cl.$^6$ ................................................. C04B 24/00
[52] U.S. Cl. ........................ 106/810; 106/802; 106/823; 427/426; 427/427
[58] Field of Search ................................... 106/728, 724, 106/802, 810, 823; 427/426, 427; 428/703

[56] References Cited

U.S. PATENT DOCUMENTS

| | | | |
|---|---|---|---|
| 3,746,557 | 7/1973 | Shimazaki et al. ................ | 106/65 |
| 3,959,093 | 5/1976 | Merkl ................................ | 204/72 |
| 4,116,706 | 9/1978 | Previte ............................. | 106/823 |
| 4,261,755 | 4/1981 | Berry et al. ...................... | 106/810 |
| 4,507,154 | 3/1985 | Burge et al. ..................... | 106/728 |
| 5,127,955 | 7/1992 | Fry et al. ......................... | 106/823 |

FOREIGN PATENT DOCUMENTS 1462729 1/1977 United Kingdom .
WO 86/03972 8/1996 WIPO .

OTHER PUBLICATIONS

WPIDS #89–219, 110 which corresponds to SU 1,435,762, Nov. 1988.
Chemical Abstracts 114:144774 (date unknown).
Chemical Abstracts 113:243291 (date unknown).
WPI Abstract Acc. No. 87–156067/22 Oct. 1986.
Copy of GB Patent Office Search Report dated 5 Feb. 1996 for GB Application No. 9524002.4.

*Primary Examiner*—Michael Marcheschi
*Attorney, Agent, or Firm*—Fish & Richardson P.C.

[57] ABSTRACT

A cement setting and hardening accelerator having the formula $$Al(OH)_x(R)_y$$

wherein R is a basic anion which is not sulphate, and x+y=3. The anion is preferably derived from an acid $RH_n$ which is preferably an organic acid. The accelerator gives excellent performance in shotcrete and is alkali-free.

20 Claims, No Drawings

CEMENT ACCELERATORS

This invention relates to accelerators for cementitious compositions and more particularly for shotcrete.

Shotcrete, concrete which is sprayed on to a substrate, must harden very quickly; typically it must have an initial set time of less than 3 minutes. Traditionally, this has been done by the use of powerful accelerators such as sodium aluminate, sodium and potassium hydroxide and certain chlorides. While conventional shotcrete accelerators such as these have delivered a satisfactory level of performance, they suffer from the problem of being caustic in nature. This makes working with shotcrete very unpleasant, leading as it does to the possibility of eye, skin and lung irritation, especially in enclosed spaces such as tunnels, and it necessitates the wearing of protective clothing which itself is unpleasant to wear in many conditions.

Attempts have been made to provide a non-caustic accelerator. One recent development has been the use of amorphous aluminium hydroxide and/or aluminium hydroxysulphate, and this has provided good results.

There is now provided according to the present invention, a cement setting and hardening accelerator having the formula $$Al(OH)_x(R)_y$$

wherein R is a basic anion which is not sulphate, and x+y=3 both x and y are greater than 0.

Provided that the conditions hereinabove referred to are observed, the nature of R is not critical. Additionally, it is possible to have a salt which has more than one type of anion R. The anion is preferably derived from an acid which may be any acid (except sulphuric acid) of the formula $RH_n$, where n is a number capable of satisfying all valencies of R. It can be, for example, a weak mineral acid, such as $H_3BO_3$ and "carbonic acid" (carbon dioxide gas dissolved in water), the latter being especially preferred. It can also be a strong mineral acid, such as hydrochloric and nitric acids (the latter being especially preferred), although there are circumstances in which hydrochloric acid would not be used because of the tendency of the chloride ion to cause corrosion (for example, when steel reinforcing bars are being used). However, the skilled person will readily recognise in which circumstances this will occur and will avoid the use of such acid.

R is preferably organic in nature. The preferred organic acids for the purposes of this invention are those which have acidity derived from the presence therein of at least one carboxyl group and/or at least one sulphonic acid group. Preferred organic anions R include those derived from methanesulphonic acid, acetic acid, propionic acid and benzoic acid, but a wide variety of other organic acids may be used, for example, lactic acid, p-toluene sulphonic acid, formic acid, and oxalic acid (optionally substituted).

The relative values of x and y depend to some extent on the nature of R, but as a general rule, the value of x is always at least 0.5, preferably at least 1.5 and most preferably at least 2.5. As a general rule, the value of y is at least 0.01 and preferably at least 0.02. Most preferably, y lies between 0.1 and 0.5. Typical examples obtained in practice are 0.27 for acetate, 0.21 for methane sulphonate, 0.55 for propionate and 0.45 for benzoate.

The accelerators according to the invention may be made by art-recognized methods, and the skilled person will readily be able to select appropriate materials and methods in every case. For example, to water in a reaction vessel are simultaneously added a solution of sodium aluminate and a solution of the acid which comprises the desired group R. This is preferably carried out at room temperature while the pH is maintained at a constant level (preferably at about 6–10, more preferably at about 6–8) throughout the preparation by adjustment of the feed rates of the alkaline aluminate and the acid. Another method which may in some cases be employed is the addition of a base to an aluminium salt, for example, the addition of sodium hydroxide to aluminium nitrate. Other methods of preparation are also possible (for example, adding a solution of one of the acid or the aluminate to a solution of the other in the reaction vessel, ), but the materials produced thereby often have a diminished level of performance. When more than one type of R is desired, a number of acids will be used, either mixed or separate. The natures of some acids may mean that a combination with certain others cannot be readily realised because of practical difficulties, but the skilled person will readily recognise this and will avoid such combinations. Precipitated salts may be separated off and washed free of alkali metal salts. Where the desired compound does not precipitate during the reaction, the compound may be recovered by using ultrafiltration, reverse osmosis, membrane filtration or some such technique to remove the alkali metal salts. The accelerators according to the invention may be dried to a powder or they may be used in the form of an aqueous suspension or solution.

The accelerators may be incorporated into cementitious compositions at a rate of from 0.1–10%, preferably from 0.5–2.5% by weight solids on cement. They may be entrained in water which is added to the cementitious composition at a spray nozzle. The invention may be used with either the wet or the dry spraying method. It is possible to use more than one such salt in the working of the invention.

The accelerators according to the invention are useful in cementitious compositions, particularly in shotcrete and sprayed mortars. The shotcrete and sprayable mortars for use with this invention may be any such materials known to the art, and they may contain all the normal admixtures found in such materials in art-recognised proportions. In all cases, the accelerators according to the invention give compositions which harden quickly on a substrate to give solid layers whose strength development is unexpectedly higher than that attainable using aluminium hydroxide. Moreover, the non-caustic nature of the materials means that the working environment is much less objectionable. The invention therefore provides a sprayable cementitious mixture which comprises an accelerating amount of a cement setting and hardening accelerator as hereinabove defined. The invention further provides a method of providing a cementitious coating on a substrate, comprising preparing a sprayable cementitious composition and spraying it on to a substrate through a nozzle, there being added to the cementitious composition at the nozzle an accelerator as hereinabove defined.

The invention is further illustrated by the following non-limiting examples.

(a) Preparation of accelerators.

To 2000 ml water in a reaction vessel are added slowly, separately and simultaneously with stirring 696 ml of a 14% (by weight) aqueous solution of propionic acid and 1000 ml of a 10% (by weight) aqueous solution of sodium aluminate. The pH is maintained at 6.5–7.5 by adjustment of addition rates, the pH being monitored by means of a pH electrode, and the temperature is maintained at 30° C. When addition of the solutions is finished, the reaction mixture is stirred for a further hour and then left overnight. The precipitate is filtered off under vacuum, washed free of alkali metal salts and dried in an oven under vacuum to yield a white amorphous powder which is found by analysis to have the formula $$Al(OH)_{2.45}(C_2H_5COO)_{0.55}$$

The preparation is repeated using one of the following acids each time instead of the propionic acid; formic acid, acetic acid, nitric acid, 4-toluenesulphonic acid, methanesulphonic acid, lactic acid and oxalic acid.

In all cases except lactic and oxalic, a precipitate is obtained. In the case of lactic and oxalic acids, the salts are water-soluble and washing is done by reverse osmosis.

The aluminium salts prepared as hereinabove described are tested in a mortar composition. The mortar composition consisted of 450 g Portland cement and 1350 CEN (European standard) sand. The water/cement ratio used is 0.5 and the workability is adjusted by using a commercially-available superplasticiser ("RHEOBILD" (trade mark) 3020 ex MBT). The aluminium salt is added and mixed in and the compressive strength of the mortar is tested 6 hours after mixing using test method DIN EN 196/1 and the results are as shown in the following table. The six-hour strength development is a particularly important parameter in shotcrete and its performance in the mortar correlates closely with its behaviour in shotcrete. For comparison, a conventional aluminium hydroxide accelerator is applied and tested under the same conditions.

| acid | % accelerator (by wt active material on cement) | Compressive Strength (N/mm$^2$) |
|---|---|---|
| acetic | 0.5 | 0.80 |
|  | 1.0 | 1.57 |
| methane sulphonic | 0.5 | 0.6 |
| boric | 0.5 | 0.72 |
| benzoic | 0.5 | 0.26 |
|  | 1.0 | 0.72 |
| aluminium hydroxide (comparison) | 0.5 | 0.23 |
|  | 1.0 | 0.70 |

In addition to obviously superior performance, the accelerators according to the invention have the same non-alkaline character as the aluminium hydroxide.

We claim:

1. A cement setting and hardening accelerator having the formula $$Al(OH)_x(R)_y$$

wherein R is a basic anion which is not sulphate, and x+y=3, wherein x and y are not 0, and wherein R is derived from an organic acid.

2. A cement setting and hardening accelerator according to claim 1, wherein R is derived from an acid RH$_n$ where n is equal to the valencies of R.

3. A cement setting and hardening accelerator according to claim 1, wherein the value of x is at least 0.5 and the value of y is at least 0.01.

4. A cement setting and hardening accelerator according to claim 3, wherein the value of x is at least 1.5.

5. A cement setting and hardening accelerator according to claim 1, wherein the value of x is at least 2.5.

6. A cement setting and hardening accelerator according to claim 1, wherein the value of y is at least 0.01.

7. A cement setting and hardening accelerator according to claim 6, wherein the value of y is at least 0.02.

8. A cement setting and hardening accelerator according to claim 6, wherein the value of y lies between 0.1 and 0.5.

9. A sprayable cementitious mixture which comprises an accelerating amount of a cement setting and hardening accelerator according to claim 1.

10. A method of applying a cementitious coating on a substrate, comprising preparing a sprayable cementitious composition and spraying it on to a substrate through a nozzle, while adding to the cementitious composition at the nozzle a cement setting and hardening accelerator according the formula $$Al(OH)_x(R)_y$$

wherein R is a basic anion which is not sulphate, and x+y=3, wherein x and y are not 0, and wherein R is derived from an organic acid.

11. A cement setting and hardening accelerator according to claim 1, wherein R is at least one organic acid selected from methanesulphonic acid, acetic acid, propionic acid, or benzoic acid.

12. A cement setting and hardening accelerator according to claim 3, wherein the value of y is at least 0.02.

13. A cement setting and hardening accelerator according to claim 12, wherein the value of y is a value between 0.1 and 0.5.

14. A method according to claim 10, wherein R is derived from an acid RH$_n$ where n is equal to the valencies of R.

15. A method according to claim 10, where in the value of x is at least 0.5 and the value of y is at least 0.01.

16. A method according to claim 15, wherein the value of x is at least 1.5.

17. A method according to claim 16, wherein the value of x is at least 2.5.

18. A method according to claim 10, wherein the value of y is at least 0.01.

19. A method according to claim 18, wherein the value of y is at least 0.02.

20. A method according to claim 19, wherein the value of y lies between 0.1 and 0.5.

* * * * *